US00RE35720E

United States Patent [19]

Arenson et al.

[11] E Patent Number: Re. 35,720

[45] Reissued Date of Patent: Feb. 3, 1998

[54] ULTRASONIC TISSUE IMAGING METHOD AND APPARATUS WITH DOPPLER VELOCITY AND ACCELERATON PROCESSING

[75] Inventors: James W. Arenson, Woodside; Ismavil M. Guracar, Redwood City; Janna G. Clark; Marc D. Weinshenker, both of Mountain View, all of Calif.

[73] Assignee: Acuson Corporation, Mountain View, Calif.

[21] Appl. No.: 601,262

[22] Filed: Feb. 14, 1996

Related U.S. Patent Documents

Reissue of:

[64] Patent No.: 5,285,788
Issued: Feb. 15, 1994
Appl. No.: 962,145
Filed: Oct. 16, 1992

[51] Int. Cl.[6] ..... A61B 8/00

[52] U.S. Cl. ..... 128/660.05; 128/662.02; 128/660.06; 128/660.07

[58] Field of Search ..... 128/660.05, 660.06, 128/660.07, 661.08, 661.09, 661.01, 662.02, 774, 916

[56] References Cited

U.S. PATENT DOCUMENTS

| | | | |
|---|---|---|---|
| 4,789,831 | 12/1988 | Mayo, Jr. . | |
| 4,830,016 | 5/1989 | Tamano et al. . | |
| 5,014,710 | 5/1991 | Maslak . | |
| 5,099,848 | 3/1992 | Parker et al. | 128/661.07 |
| 5,105,817 | 4/1992 | Uchibori et al. . | |
| 5,165,413 | 11/1992 | Maslak et al. | 128/660.05 |
| 5,190,044 | 3/1993 | Kawasaki et al. | 128/661.09 |
| 5,197,477 | 3/1993 | Peterson et al. | 128/661.08 |
| 5,409,010 | 4/1995 | Beach et al. | 128/661.09 |

FOREIGN PATENT DOCUMENTS

| | | |
|---|---|---|
| 2-193650 | 1/1989 | Japan . |
| WO 86/03593 | 6/1986 | WIPO . |

OTHER PUBLICATIONS

Federal Circuit Decision, *O.I. Corp. v. Tekmar Co.*, (96–1427, May 22, 1997).

Federal Circuit Decision, *Serano v. Telular Corp.*, 996–1308, Apr. 25, 1997).

"Colour Doppler Velocity Imaging of the Myocardium" by W. N. McDicken, G. R. Sutherland, et al., in *Ultrasound in Medicine and Biology*, vol. 18, Nos. 6/7, 1992.

"Computer Based Pattern Recognition of Carotid Arterial Disease Using Pulsed Doppler Ultrasound" by F. M. Greene, et al., in *Ultrasound in Medicine and Biology*, vol. 8, No. 2, 1982.

*Primary Examiner*—George Manuel
*Attorney, Agent, or Firm*—Brinks Hofer Gilson & Lione

[57] ABSTRACT

An ultrasound tissue imaging system having an acoustic transducer, B-mode imaging means to produce with said transducer an electronically scanned B-mode image of tissue under examination. Doppler imaging means that accepts and processes large amplitude, low frequency signals to produce with said transducer an electronically scanned acoustic image of moving tissue, and color display means for displaying the B-mode image as a two-dimensional image with echo intensities encoded using a first mapping function and for simultaneously displaying Doppler information from moving tissue as a two-dimensional image using a second and distinct mapping function that is spatially coordinated with and superimposed upon said B-mode image to augment the B-mode image.

34 Claims, 4 Drawing Sheets

ULTRASONIC TISSUE IMAGING METHOD AND APPARATUS WITH DOPPLER VELOCITY AND ACCELERATON PROCESSING

Matter enclosed in heavy brackets [ ] appears in the original patent but forms no part of this reissue specification; matter printed in italics indicates the additions made by reissue.

BACKGROUND OF THE INVENTION

In B-mode medical ultrasound imaging, the scanner transmits ultrasonic bursts into the body and detects the energy of ultrasonic echoes backscattered from both stationary and moving tissues in the body. Ultrasonic scanners may also offer two dimensional Doppler flow detection (also referred to as color Doppler imaging) to detect and image moving blood. Recently, some investigators have proposed using color Doppler blood flow imaging capabilities to image moving structures other than blood, for example the moving heart structure.

In B-mode imaging, stationary and moving targets are both imaged. Often these images are degraded by the presence of stationary noise or clutter from both electrical sources and acoustic sources. In cardiac ultrasound applications, the moving myocardium is of principal interest, and can be obscured by stationary noise detected with B-mode imaging. Color Doppler imaging methods will remove this stationary clutter but cannot detect moving myocardium with the required sensitivity and specificity, since Doppler processing has been optimized for detecting blood velocities and not slower moving myocardium. The characteristics of ultrasonic signals returning from moving myocardium are different from those signals returning from blood. For example, in blood flow detection, the processor recognizes echoes from the strong, slow moving heart tissue as clutter and removes them from the image by means of a stationary target canceller or a high pass filter or both. Such a high pass filter is illustrated in the system described in U.S. Pat. No. 5,014,710 entitled "Steered Linear Color Doppler Imaging" for the color Doppler path. It is precisely those strong, slow moving targets that correspond to moving myocardium, but they, too, are removed from the color Doppler image. Therefore, prior art color Doppler imaging systems have had difficulty imaging slow moving myocardium.

SUMMARY OF THE INVENTION

An ultrasound tissue imaging system having an acoustic transducer, B-mode imaging means to produce with said transducer an electronically scanned B-mode image of tissue under examination, Doppler imaging means that accepts and processes large amplitude, low frequency signals to produce with said transducer an electronically scanned acoustic image of moving tissue and color display means for displaying the B-mode image as a two-dimensional image with echo intensities encoded using a first mapping function and for simultaneously displaying Doppler information from moving tissue as a two-dimensional image using a second and distinct mapping function that is spatially coordinated with and superimposed upon said B-mode image to augment the B-mode image.

The present invention images moving tissue with color Doppler imaging means that has the new features of removing or bypassing the circuit that rejects stationary or slow moving targets and of modifying the processing circuits so that they can detect large amplitude, low frequency signals. The invention provides new color maps that color both forward and reverse motion in the same way, as well as Doppler grey-scale maps. In one mode, the invention calculates acceleration from Doppler velocity information and displays that color mapped acceleration of moving tissue. Combining the detected Doppler signals from moving tissue with a B-mode signal augments the B-mode image of moving tissue or, alternatively, gating the B-mode signal with the detected Doppler signals from moving tissue may be used to block stationary tissue and clutter signals from the B-mode image.

BRIEF DESCRIPTION OF PRIOR ART COLOR DOPPLER IMAGING SYSTEMS

Figure 1:
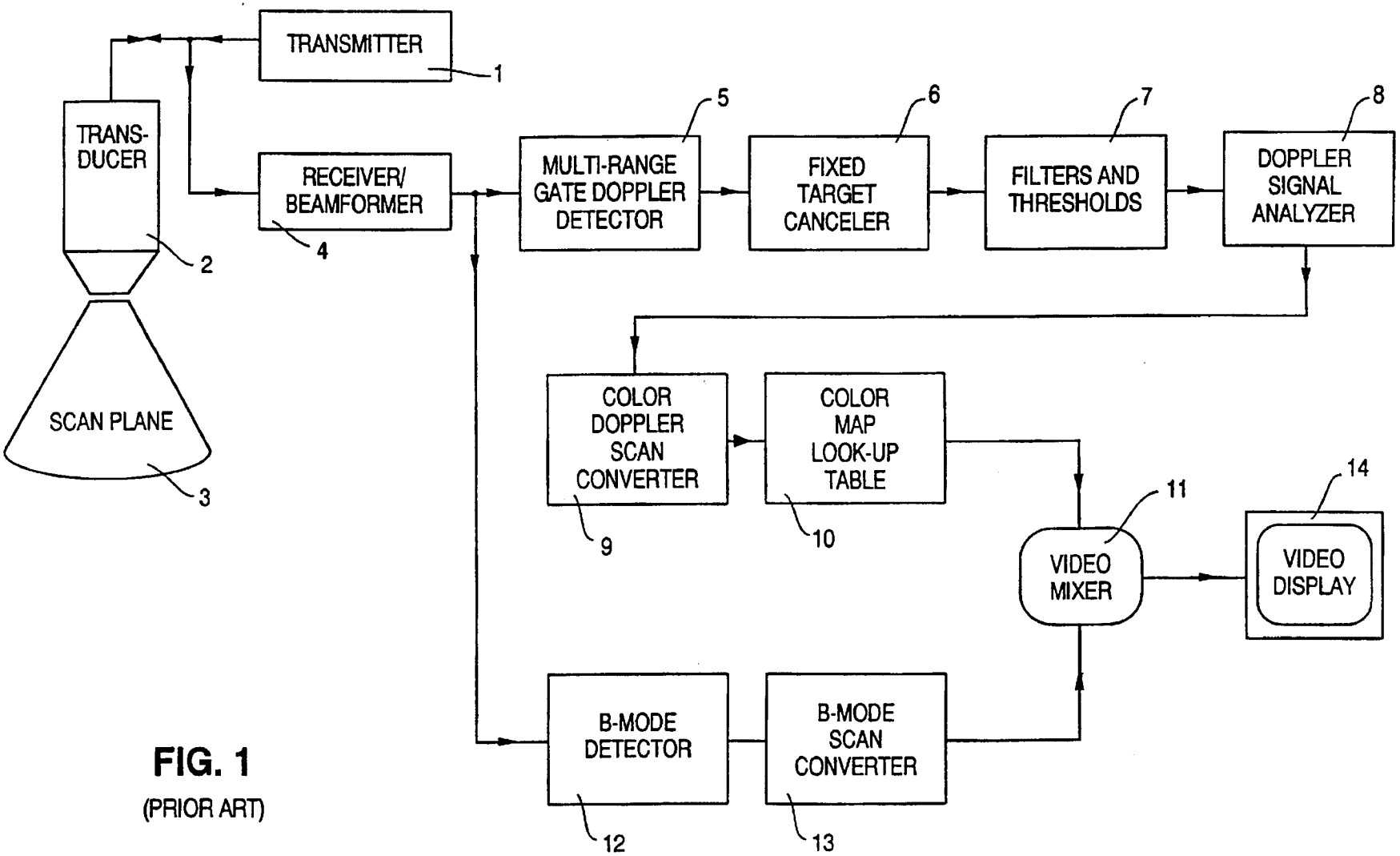
FIG. 1 (PRIOR ART)
FIG. 1 is the block diagram of a typical color Doppler imaging system useful for color blood flow display.

FIG. 1 is the block diagram of a color Doppler imaging system similar to that described in U.S. Pat. No. 5,014,710 entitled "Steered Linear Color Doppler Imaging" issued May 14, 1991, which by reference is a part of this description. The transmitter 1 excites the acoustic transducer 2 which propagates ultrasonic energy bursts into the body on a scan plane 3. The transducer 2 usually comprises a phased array of acoustic transducer elements. Returning ultrasonic echoes are transduced into electrical signals that are amplified and focused by means of receiver/beamformer 4.

The received electrical signals are processed in one path by Doppler imaging means including a multi-range gate Doppler detector 5, a processor that detects the Doppler shifted signals at multiple positions along each of a plurality of ultrasound scan lines. These signals are then passed through a circuit designated fixed target canceller 6 that removes non-Doppler shifted signals corresponding to stationary clutter. Filters and thresholds are then applied at 7 for conditioning the signal to remove artifactual and clutter signals from the Doppler blood flow signals. Then the Doppler frequencies are analyzed in a Doppler frequency analyzer 8 and a number of parameters (including mean, standard deviation and energy) are estimated for the multiple positions along the ultrasound scan line as is more particularly described in U.S. Pat. No. 5,014,710.

This analyzed Doppler information is stored for each line in color Doppler scan converter 9 along with additional information from other ultrasound scan lines, comprising a complete two-dimensional color Doppler scan frame. The scan converter 9 also translates or converts the Doppler information collected along the multiple ultrasound scan lines to a rectangular raster required for conventional video displays. A color is assigned to each position in the scan frame, according to the frequency characteristics detected at that position by reference to color map look-up table 10. The color mapping considers mean frequency, standard deviation or energy, in combination or alone, as specified by the user.

The video mixer 11 combines the color Doppler information with B-mode information acquired by B-mode imaging means in a second path including the B-mode detector 12 and scan converter 13. The video mixer presents a combined video signal for display to the video monitor 14.

BRIEF DESCRIPTION OF A PREFERRED EMBODIMENT OF THE INVENTION

Figure 2:
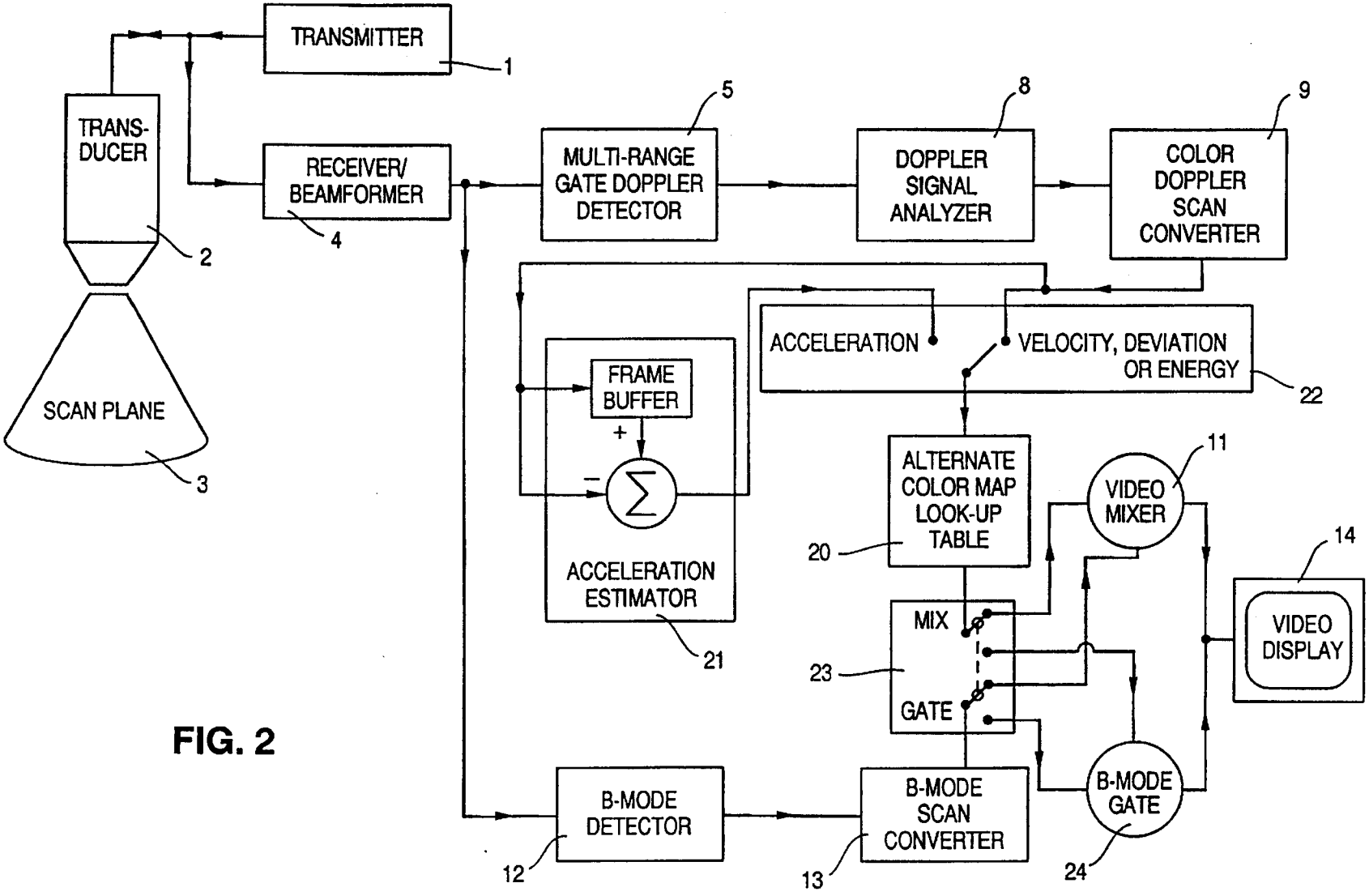
FIG. 2 is a block diagram of the color Doppler tissue imaging system of this invention.

FIG. 2 is the block diagram of the color Doppler tissue imaging system of this invention including the B-mode and color Doppler imaging means of FIG. 1. But, here, the fixed target canceller 6 and filters and thresholds 7 are removed from the system of FIG. 1. Alternate color look-up tables 20 are provided. An acceleration estimator 21 estimates acceleration, for example, by subtracting data in the current velocity scan frame from the previous velocity scan frame in response to switch means 22. The color or grey-scale assigned to each position in the scan frame in a first mode of operation controlled by switch means 23 is mixed with B-mode information from B-mode scan converter 12 and presented to the display monitor 14.

The switch means 22 also controls a second mode of operation that gates B-mode information to the display 14 only when a color Doppler signal is detected. A gate function 24 is shown schematically where the B-mode signal is gated from B-mode scan converter 13 and allowed through to the video display 14 only when a color Doppler signal is detected.

Figure 3C:
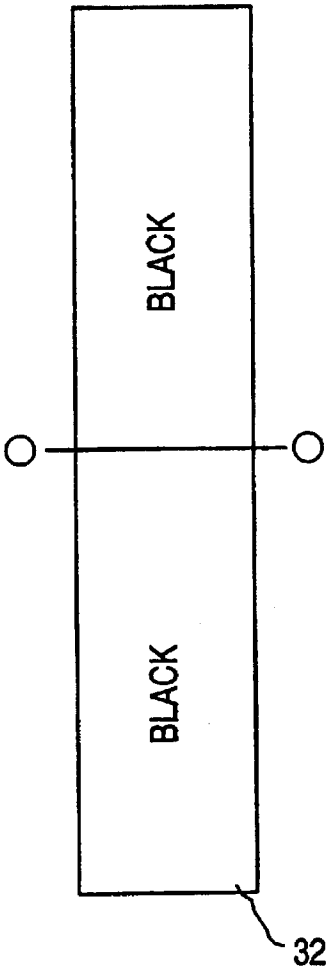
FIG. 3 illustrates alternative color and other look-up tables useful in the invention illustrated in FIG. 2.
Figure 3B:
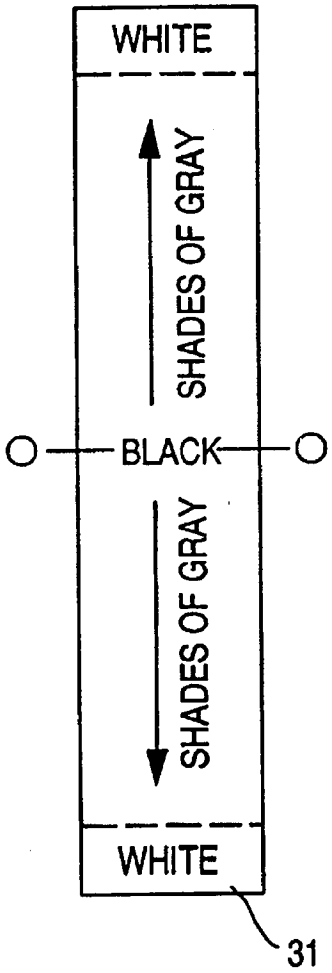
Figure 3A:
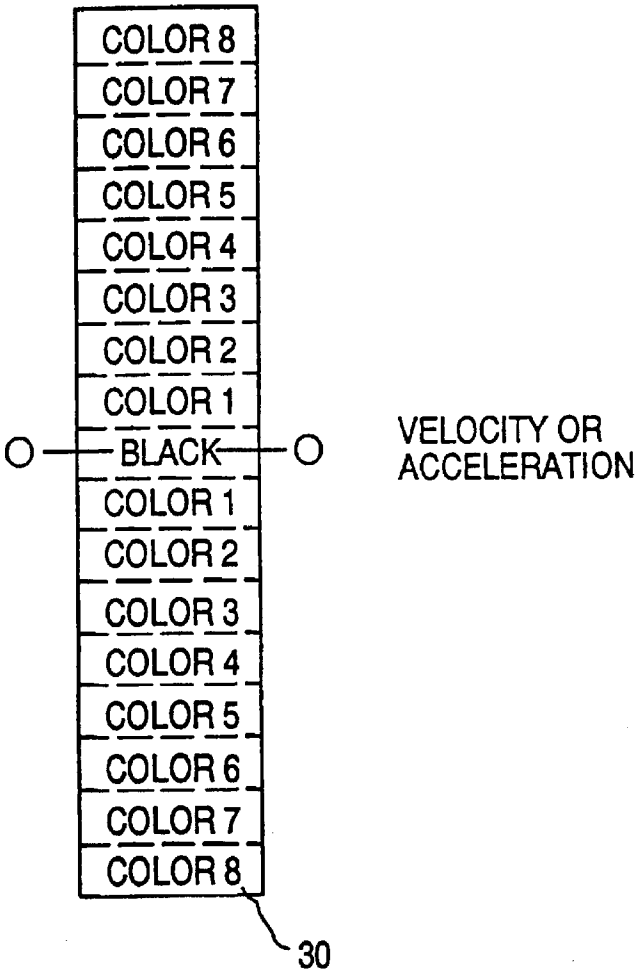

FIG. 3 shows alternate look-up tables. The first look-up table 30 shows a symmetric color distribution, thereby mapping colors based on the magnitude of the Doppler shift, rather than direction typically used in color flow mapping. The second look-up table 31 shows a gray scale distribution, which is useful when mixed with a conventional B-mode gray scale image to enhance or augment the myocardium as in FIG. 5. The third look-up table 32 is made up entirely of black and is used along with the gate function 24. In this option, the B-mode pixels are combined in the video mixer with the corresponding black color Doppler pixels, thereby producing the B-mode image with only the moving tissues displayed.

Figure 4:
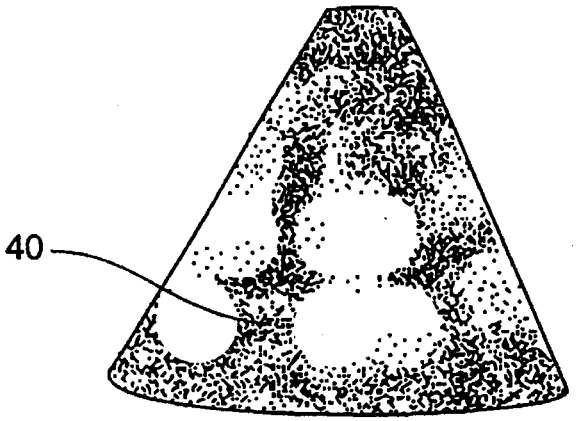
FIG. 4 illustrates a B-mode image of the heart and other tissue with superimposed clutter and noise.
Figure 5:
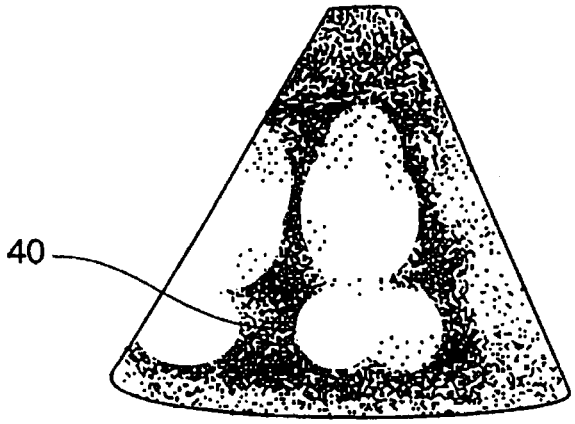
FIG. 5 is a B-mode image of the heart with the moving myocardium enhanced by the color Doppler means of this invention.
Figure 6:
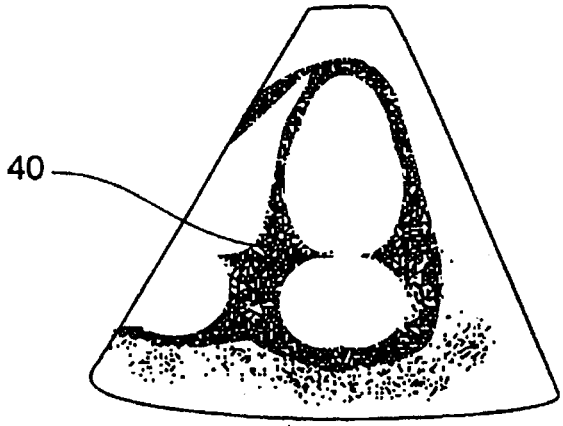
FIG. 6 is a B-mode image of the heart with stationary tissue and clutter removed by the Doppler gated system of this invention.

FIG. 4 shows a conventional B-mode echocardiogram where the myocardium image 40 is surrounded by other tissue and superimposed clutter and noise 41. FIG. 5 shows a B-mode echocardiogram with the moving myocardium 40 enhanced by this invention. FIG. 6 shows a B-mode echocardiogram where the stationary tissue and clutter has been removed by the gate function 24 of this invention to display only the myocardium image 40.

The clinician's scanning technique with this invention is similar to conventional B-mode image acquisition. When the appropriate scan plane has been achieved, the tissue motion detection mode can begin by pressing the appropriate key on the front panel. Moving tissue structures then will be superimposed on the video display, along with the conventional B-mode image.

The user can select a number of different operating conditions. For example, the user can choose to image either the velocities, standard deviations, energies or accelerations of the moving tissue by switch means 22. The user can select either conventional color maps 10 to encode the direction as well as the magnitudes of the velocities or accelerations, or use the symmetric, non-directional color maps 20. The user can select a grey-scale "color" map 31 for the motion information and combine this with the B-mode information. Alternatively, the user can color the B-mode image and combine it with either a gray or color coded motion image. The clinician can also remove the underlying B-mode information (by reducing the B-mode gain), and image only the color Doppler information. Also, the user can select a "gated" B-mode operation by switch means 23 where only the B-mode information from moving tissue is imaged as in FIG. 6. In this case, the B-mode image is displayed only if a Doppler signal is detected at the corresponding location in the image. Alternatively, the B-mode could be gated by the absence of a Doppler signal, thereby enhancing the boundary between the myocardium and the surrounding tissue.

Stationary targets can be removed through the use of color maps, where the lowest velocities are assigned no color. Further, the range of velocities can be changed in the same way as with conventional color Doppler imaging by adjusting the sampling rate of the Doppler information.

In the strict sense, acceleration detection looks for differences in the velocities from one time frame to the next. In the case where same velocities are detected in the two adjacent time frames, there will be no acceleration measured. For moving tissue imaging, this loss of signal is distracting and counterintuitive. Therefore, for these operating cases, the acceleration processor will assign a low value of acceleration, instead of zero acceleration. The resulting image, while not truly displaying acceleration, has more diagnostic information. In the case where the velocities are zero in adjacent time frames, the acceleration is also assigned to zero.

Although this invention is described in the context of two-dimensional Doppler processing methods, this processing is also applicable to color M-mode operation. Tissue motion can be displayed in conjunction with a conventional M-mode display in similar ways as described for two-dimensional imaging.

Advantages of this invention over what has been done before include:

1. Slow moving targets corresponding to moving myocardium can be detected with better sensitivity. Clinically, this additional information assists in determining cardiac wall motion characteristics.

2. In some instances, acceleration mapping is more sensitive to myocardial motion than velocity mapping. For example, at end-diastole/onset-of-systole the myocardium stops and reverses direction. At this time the velocities are either zero or very low. However, the accelerations can be quite high at these times. Acceleration mapping presents motion information throughout more of the cardiac cycle, and generates images with greater clarity and sensitivity than those available with velocity imaging.

3. With the gated B-mode operation, stationary noise and clutter can be removed from the image.

4. The detection of endocardium is facilitated by a combination of reducing the stationary clutter in the blood pools and enhancing the moving myocardium.

5. This invention facilitates the detection of the pericardium in those views where the tissue adjacent to the myocardium is stationary.

6. This invention facilitates the detection of the myocardium wall thickness.

7. In the context of moving myocardium, magnitude color Doppler mapping is simpler to interpret than directional color Doppler mapping.

8. As the myocardium is augmented with this invention, both manual and automatic detection of blood pool/myocardium borders is enhanced.

Although this method has been described on one type of color Doppler imaging apparatus based on autocorrelation methods, it could be done on other systems, including other types of two-dimensional flow estimators. The symmetric color maps could be replaced by using conventional color maps with non-directional Doppler detection. The acceleration calculation can be done by means other than subtraction of adjacent velocity frames, and still provide the same information.

Other variations in the invention as defined in the following claims will be apparent to those skilled in the ultrasound imaging art.

We claim:

1. An ultrasound tissue imaging system having an acoustic transducer and comprising B-mode imaging means to produce with said transducer an electronically scanned B-mode image of tissue under examination, said B-mode image substantially representing the intensity of echoes returned from said tissue along multiple B-mode scan lines;

Doppler imagine means that accepts and processes large amplitude, low frequency signals to produce with said transducer an electronically scanned Doppler image of said moving tissue, the Doppler image representing estimates of velocity including means, standard deviation or energy derived from Doppler-shifted echoes reflected from said moving tissue at multiple sample volumes along multiple Doppler scan lines;

color display means for displaying the B-mode image as a two-dimensional image with echo intensities encoded using a first mapping function and for augmenting the B-mode image by simultaneously displaying said estimates of velocity, as a two-dimensional Doppler image using a second and distinct mapping function that is spatially coordinated with and superimposed upon said b-mode image.

2. The system of claim 1 further comprising means for estimating acceleration from said estimates of velocity and means for displaying estimates of that acceleration as the two-dimensional Doppler image using said second mapping function.

3. The system of claim 1 wherein the B-mode image is gated to the display by gate means only upon detection of said acquired and processed Doppler information so as to remove stationary noise and clutter.

4. The system of claim 1 wherein the second mapping function color maps the magnitude of forward and reverse motion without distinguishing direction of the motion.

5. The system of claim 1 wherein the second mapping function grey-scale maps the Doppler information.

6. A method of forming a composite B-mode and color Doppler acoustic image of moving tissue by transmitting acoustic pressure waves and receiving returned echoes on acoustic lines scanned by a transducer, said method comprising the steps of deriving a B-mode image from echoes received along a first set of image scan lines, acquiring and processing color Doppler information at large amplitude and low frequencies from said moving tissue at multiple volumes along scan lines that are the same as or propagated independently from the B-mode scan lines and displaying said color Doppler information as a two-dimensional color coded image of moving tissue that is spatially coordinated with and superimposed upon said B-mode image.

7. The method of claim 6 wherein the step of acquiring and processing color Doppler information further includes deriving estimates of acceleration for Doppler shifted echoes and displaying those estimates as the two-dimensional color coded image of said moving tissue.

8. The method of claim 6 wherein the display of said B-mode image is gated by said color Doppler information.

9. An ultrasound tissue imaging system having an acoustic transducer and comprising B-mode imaging means to produce with said transducer an electronically scanned B-mode image of tissue under examination, said B-mode image substantially representing the intensity of echoes returned from said tissue along multiple B-mode scan lines;

imaging means that accepts and processes large amplitude, low frequency signals to produce with said transducer an electronically scanned Doppler image of said moving tissue, the image representing estimates of velocity derived from echoes reflected from said moving tissue at multiple sample volumes along multiple scan lines;

color display means for displaying the B-mode image as a two-dimensional image with echo intensities encoded using a first mapping function and for augmenting the B-mode image by simultaneously displaying said estimates of velocity as a two-dimensional Doppler image using a second and distinct mapping function that is spatially coordinated with and superimposed upon said B-mode image.

10. The system of claim 9 further comprising means for estimating acceleration from said estimates of velocity and means for displaying estimates of that acceleration as the two-dimensional image using said second mapping function.

11. The system of claim 10 wherein the second mapping function color maps at a low non-zero value estimates of acceleration derived from estimates of velocity when those velocities are the same but also are non-zero.

12. The system of claim 9 wherein the blood pool/myocardium borders are enhanced by gating the B-mode image to the display means only in the presence of acquired and processed Doppler information.

13. A method of forming a color Doppler acoustic image of moving tissue by transmitting acoustic pressure waves and receiving returned echoes on acoustic lines scanned by a transducer, said method comprising the steps of acquiring and processing color Doppler information at large amplitude and low frequencies from said moving tissue at multiple volumes along a plurality of scan lines and displaying said color Doppler information as a two-dimensional color coded image of said moving tissue.

*14. The method of claim 13 wherein said displaying step displays said color Doppler information by assigning no color to color Doppler information associated with a lowest velocity.*

*15. The method of claim 14 further comprising the step of varying a sampling rate of the color Doppler information in the acquiring and processing step.*

*16. The method of claim 13 wherein said acquiring and processing step comprises the step of supplying an output signal of a Doppler detector to a Doppler signal analyzer without filtering between the Doppler detector and the Doppler signal analyzer.*

*17. The method of claim 6 or 13 wherein the Doppler information comprises Doppler energy information.*

*18. The method of claim 6 or 13 wherein the Doppler information comprises Doppler acceleration information.*

*19. The system of claim 1 or 9 wherein the second mapping function assigns no color to a lowest estimate of velocity.*

*20. The method of claim 6 wherein said acquiring and processing step processes color Doppler information indicative of velocity of said moving tissue, and wherein said displaying step comprises the step of assigning no color to portions of the image associated with moving tissue having a lowest velocity.*

*21. The method of claim 20 further comprising the step of varying a sampling rate of the color Doppler information in the acquiring and processing step.*

*22. An ultrasound tissue imaging system having an acoustic transducer and comprising:*

*a receiver/beamformer coupled to the transducer;*

*a Doppler detector coupled to the receiver/beamformer;*

*a Doppler signal analyzer coupled to the Doppler detector without filtering between the Doppler detector and the Doppler signal analyzer, said Doppler signal analyzer processing color Doppler information at large amplitude and low frequencies from moving tissue at multiple volumes along a plurality of scan lines; and*

*a display system coupled to the Doppler signal analyzer, said display system operative to display said color Doppler information as a two-dimensional color coded image of said moving tissue.*

*23. The system of claim 22 wherein the display system comprises a color mapping function that assigns no color to the volumes characterized by a lowest velocity.*

*24. An ultrasound tissue imaging system having an acoustic transducer and comprising:*

*means for acquiring and processing color Doppler information at large amplitude and low frequencies from moving tissue at multiple volumes along a plurality of scan lines; and*

*means for displaying said color Doppler information as a two-dimensional color coded image of said moving tissue.*

*25. The system of claim 24 wherein said means for acquiring and processing comprises:*

*a receiver/beamformer coupled to the transducer;*

*a Doppler detector coupled to the receiver/beamformer; and*

*a Doppler signal analyzer coupled to the Doppler detector without filtering between the Doppler detector and the Doppler signal analyzer.*

*26. The system of claim 24 wherein the display means comprises means for assigning no color to the volumes characterized by a lowest velocity.*

*27. A method for displaying a B-mode image of moving tissue by transmitting acoustic pressure waves and receiving returned echos on acoustic lines scanned by a transducer, said method comprising the following steps:*

*deriving a B-mode image from echoes received along a first set of image scan lines;*

*acquiring Doppler information from said moving tissue at multiple volumes along scan lines that are the same as or propagated independently from the B-mode scan lines; and*

*gating the B-mode image with the Doppler information.*

*28. The method of claim 27 comprising the further step of displaying the gated B-mode image.*

*29. The method of claim 27 wherein the acquiring step comprises the step of acquiring and processing Doppler information at large amplitude and low frequencies from said moving tissue.*

*30. An ultrasound tissue imaging system having an acoustic transducer and comprising:*

*a receiver/beamformer coupled to the transducer;*

*a B-mode imaging system operative with the transducer to produce electronically scanned B-mode image information of tissue under examination;*

*a Doppler information acquiring system operative with the transducer to acquire Doppler information from said tissue;*

*a B-mode gate responsive to the B-mode imaging system and to the Doppler information acquiring system to produce a gated output signal, wherein the gated output signal corresponds to the B-mode image information gated by the Doppler information.*

*31. The system of claim 30 further comprising a display coupled to the B-mode gate to display the gated output signal.*

*32. The system of claim 30 wherein the Doppler information acquiring system comprises a Doppler detector and a Doppler signal analyzer coupled to the Doppler detector without any substantial filtering therebetween, said Doppler signal analyzer being responsive to large amplitude, low frequencies signals from said tissue.*

*33. The system of claim 22, 24 or 30 wherein the Doppler information comprises Doppler energy information.*

*34. The system of claim 22, 24 or 30 wherein the Doppler information comprises Doppler acceleration information.*

* * * * *

UNITED STATES PATENT AND TRADEMARK OFFICE

CERTIFICATE OF CORRECTION

PATENT NO. : Re. 35,720
DATED : February 3, 1998
INVENTOR(S) : James W. Arenson et al.

It is certified that error appears in the above-indentified patent and that said Letters Patent is hereby corrected as shown below:

On the Title Page

Item [54] and col. 1, line 3, replace "ACCELERATON" with --ACCELERATION--.

In item[75], line 5, replace "Ismavil" with --Ismayil--.

In item [56], line 4, under "OTHER PUBLICATIONS" replace "996" with --(996--.

Signed and Sealed this

Twenty-third Day of March, 1999

*Attest:*

Q. TODD DICKINSON

*Attesting Officer*

*Acting Commissioner of Patents and Trademarks*